United States Patent [19]

Taketomi et al.

[11] Patent Number: 5,210,332
[45] Date of Patent: May 11, 1993

[54] IRIDIUM-OPTICALLY ACTIVE PHOSPHINE COMPLEX AND PROCESS FOR PRODUCING OPTICALLY ACTIVE ALCOHOLS USING THE SAME

[75] Inventors: Takanao Taketomi; Susumu Akutagawa; Hidenori Kumobayashi, all of Tokyo; Hidemasa Takaya, Shiga; Kazushi Mashima, Kyoto, all of Japan

[73] Assignee: Takasago International Corporation, Tokyo, Japan

[21] Appl. No.: 856,403

[22] Filed: Mar. 20, 1992

Related U.S. Application Data

[62] Division of Ser. No. 769,280, Oct. 1, 1991.

[30] Foreign Application Priority Data

Oct. 1, 1990 [JP] Japan ................... 2-263439

[51] Int. Cl.$^5$ ............................. C07C 33/28
[52] U.S. Cl. ............................. 568/813; 568/614
[58] Field of Search ............... 556/136; 568/813, 814

[56] References Cited

U.S. PATENT DOCUMENTS 4,924,029 5/1990 Harsy .................. 568/813

FOREIGN PATENT DOCUMENTS 0104376 4/1984 European Pat. Off. .
0245959 11/1987 European Pat. Off. ........... 568/813
1135979 12/1968 United Kingdom ............... 568/813

*Primary Examiner*—Werren B. Lone
*Attorney, Agent, or Firm*—Sughrue, Mion, Zinn, Macpeak & Seas

[57] ABSTRACT

An iridium-optically active phosphine complex represented by formula (I):

$$[H_2Ir(L^1)(L^2)]Y \qquad (I)$$

wherein $L^1$ represents an optically active phosphine compound represented by formula (II):

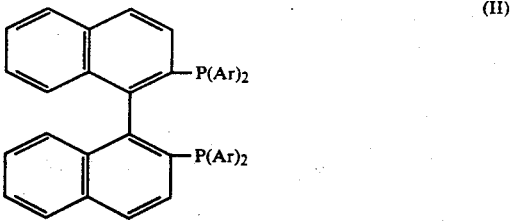

wherein Ar represents a phenyl group or a p- and/or m-lower alkyl-substituted phenyl group, or formula (III):

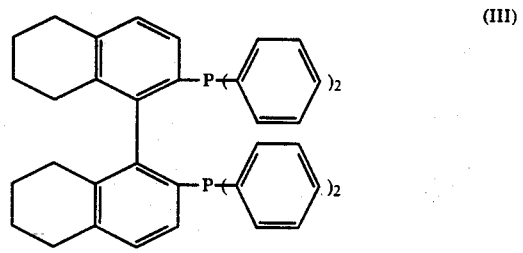

$L^2$ represents a tertiary phosphine compound represented by formula (IV):

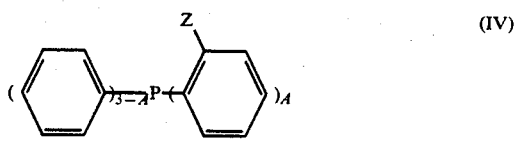

wherein Z represents a lower alkoxy group or a di-lower alkylamino group; and A represents an integer of from 1 to 3; Y represents $BF_4$, $PF_6$, $ClO_4$, or $BPh_4$, wherein Ph represents a phenyl group, and a process for producing an optically active alcohol using the above complex as an enantioselective catalyst are disclosed. The complex exhibits excellent catalytic activity to give high enantioselective yields in enantioselective synthesis, particularly enantioselective hydrogenation.

8 Claims, No Drawings

IRIDIUM-OPTICALLY ACTIVE PHOSPHINE COMPLEX AND PROCESS FOR PRODUCING OPTICALLY ACTIVE ALCOHOLS USING THE SAME

This is a divisional of application Ser. No. 07/769,280 filed Oct. 1, 1991.

FIELD OF THE INVENTION

The present invention relates to a novel iridium-phosphine complex useful as a calalyst for various organic syntheses, particularly enantioselective hydrogenation reactions and to a process for producing optically active alcohols using the same.

BACKGROUND OF THE INVENTION

A number of organic synthesis reactions using a transition metal complex as a catalyst have hitherto been developed and made use of for various purposes. In particular, many reports have been made on enantioselective catalysts useful for enantioselective synthesis reactions, such as enantioselective hydrogenation and enantioselective isomerization. Among them, metal complexes in which an optically active tertiary phosphine compound is coordinated to metallic rhodium or ruthenium are well known as catalysts for enantioselective hydrogenation.

For example, a rhodium-phosphine complex using 2,2'-bis(diphenylphosphino)-1,1'-binaphthyl (hereinafter abbreviated as BINAP) as a ligand is disclosed in JP-A-55-61937 (the term "JP-A" as used herein means an "unexamined published Japanese patent application").

Known ruthenium complexes include those having BINAP or a derivative thereof as a ligand, such as $Ru_2Cl_4(BINAP)_2(NEt_3)$ (wherein Et represents an ethyl group) as disclosed in Ikariya, et al., *J. Chem. Soc., Chem. Commun.*, p. 922 (1985), $Ru(O_2CR)_2\text{-}(BINAP)$ (wherein R represents a lower alkyl group, a lower alkyl-substituted phenyl group, etc.) as disclosed in JP-A-62-265293, and $[RuH_l(R\text{-}BINAP)_m]X_n$ (wherein R represents a hydrogen atom or a methyl group; X represents $ClO_4$, $BF_4$, or $PF_6$; when l is 0, m represents 1, and n represents 2; and when l is 1, m represents 2, and n represents 1) as disclosed in JP-A-63-41487.

For further reference to enantioselective synthesis reactions using transition metal catalysts, Sheri. L. Blystone, *Chemical Reviews*, pp. 1663–1679 (1989) can be referred to.

However, few cases are known in which an iridium-optically active phosphine complex is actually used as a catalyst for enantioselective syntheses, except conversion of an imine to an optically active amine as reported, e.g., in JP-A-63-57558 and JP-A-64-47723.

Rhodium- or ruthenium-optically active phosphine complexes are known to exhibit high catalytic activity on a relatively wide range of substrates to give a high enantioselectivity (i.e., optical purity of a product) in enantioselective syntheses, especially enantioselective hydrogenation. However, both catalytic activity and enantioselectivity achieved by these complexes are sometimes unsatisfactory depending on the reaction substrate. Accordingly, it has been demanded to develop a novel catalyst for enantioselective syntheses.

SUMMARY OF THE INVENTION

In order to meet the above-described demand in the art, the inventors have conducted extensive studies and, as a result, have found a novel iridium-optically active phosphine complex which exhibits excellent catalytic activity and gives high enantioselective yields in enantioselective syntheses, particularly enantioselective hydrogenation. The present invention has been completed based on this finding.

The present invention relates to an iridium-optically active phosphine complex represented by formula (I):

$$[H_2Ir(L^1)(L^2)]Y \qquad (I)$$

wherein $L^1$ represents an optically active phosphine compound represented by formula (II):

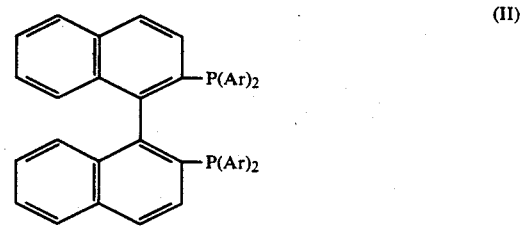

wherein Ar represents a phenyl group or a p- and/or m-lower alkyl-substituted phenyl group (the lower alkyl moiety thereof preferably containing from 1 to 4 carbon atoms), or formula (III):

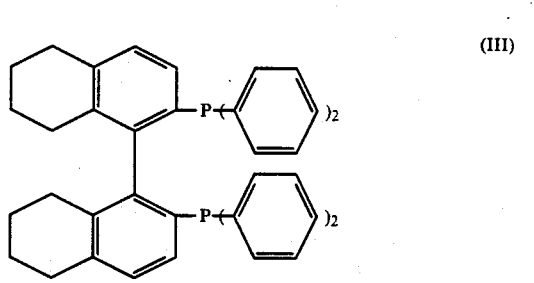

$L^2$ represents a tertiary phosphine compound represented by formula (IV):

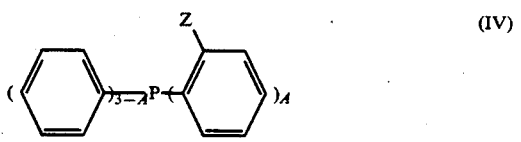

wherein Z represents a lower alkoxy group or a di-lower alkylamino group (the lower alkoxy or lower alkyl moiety thereof preferably containing from 1 to 4 carbon atoms); and A represents an integer of from 1 to 3;

Y represents $BF_4$, $PF_6$, $ClO_4$, or $BPh_4$, wherein Ph represents a phenyl group.

The present invention also relates to a process for producing an optically active 3-hydroxytetrahydrothiophene comprising enantioselectivly hydrogenating 3-oxotetrahydrothiophene in the presence of the iridium-optically active phosphine complex represented by formula (I).

The present invention further relates to a process for producing an optically active allyl alcohol derivative represented by formula (VI):

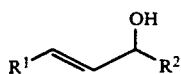

(VI)

[wherein $R^1$ and $R^2$ each represent an aromatic hydrocarbon group or an aliphatic hydrocarbon group], comprising enantioselective hydrogenation of an $\alpha,\beta$-unsaturated ketone represented by formula (V):

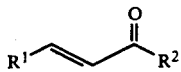

(V)

wherein $R^1$ and $R^2$ are as defined above, in the presence of the iridium-optically active phosphine complex represented by formula (I).

DETAILED DESCRIPTION OF THE INVENTION

In formula (I), the optically active phosphine compound represented by $L^1$ includes 2,2'-bis(diphenylphosphino)-1,1'-binaphthyl, 2,2'-bis(di-p-tolylphosphino)-1,1'-binaphthyl (hereinafter abbreviated as Tol-BINAP), 2,2'-bis(di-m-tolylphosphino)-1,1'-binaphthyl, 2,2'-bis(di-3,5-dimethylphenylphosphino)-1,1'-binaphthyl, 2,2'-bis(di-p-chlorophenylphosphino)-1,1'-binaphthyl, and 2,2'-bis(di-p-t-butylphenylphosphino)-1,1'-binaphthyl. The tertiary phosphine compound represented by $L^2$ includes bis(o-dimethylaminophenyl)phenylphosphine, tris(o-dimethylaminophenyl)phosphine, o-dimethylaminophenyldiphenylphosphine, bis(o-methoxyphenyl)phenylphosphine, o-methoxyphenyldiphenylphosphine, tris(o-methoxyphenyl)phosphine, bis(o-ethoxyphenyl)phenylphosphine, o-ethoxyphenyldiphenylphosphine, bis(o-diethylaminophenyl)phenylphosphine, and o-diethylaminophenyldiphenylphosphine.

The iridium-optically active phosphine complex of formula (I) can be prepared, for example, according to the following reaction scheme.

[Ir(COD)(CH$_3$CN)$_2$]Y      (VII)

↓ $L^1$

[Ir(COD)($L^1$)]Y      (VIII)

↓ $L^2$
↓ $H^2$

[H$_2$Ir($L^1$)($L^2$)]Y      (I)

wherein COD represents 1,5-cyclooctadiene; and $L^1$, $L^2$, and Y are as defined above.

That is, a complex of formula (VII) is reacted with an optically active phosphine compound $L^1$ to obtain a complex of formula (VIII), which is then reacted with a tertiary phosphine compound $L^2$ and hydrogen to obtain the iridium-optically active phosphine complex (I) of the present invention.

The starting complex (VII) can be prepared according to the process disclosed in M. Green, et al., *J. Chem. Soc.*, (A) 2334 (1971).

Of the starting optically active phosphine compounds $L^1$, the optically active compound of formula (III), i.e., 2,2'-bis(diphenylphosphinyl)-5,5',6,6',7,7',8,8'-octahydro-1,1'-binaphthyl (hereinafter abbreviated as OcH-BINAP) can be synthesized, for example, as follows. 2,2'-Dibromo-1,1'-binaphthyl synthesized by the process disclosed in H. Takaya, et al., *J. Orc. Chem.*, Vol. 51, p. 629 (1986) is hydrogenated in the presence of a ruthenium-on-carbon catalyst to obtain 2,2'-dibromo-5,5',6,6',7,7',8,8'-octahydro-1,1'-binaphthyl (2,2'-dibromo-1,1'-bitetrahydronaphthalene), which is then reacted with metallic magnesium to form a Grignard reagent. The resulting Grignard reagent is condensed with diphenylphosphinyl chloride to synthesize racemic OcH-BINAP. The racemate is optically resolved by recrystallization from a mixed solvent of chloroform and ethyl acetate in the presence of optically active dibenzoyltartaric acid as a resolving agent, and the precipitated crystal collected by filtration is treated with 1N sodium hydroxide to obtain a phosphine oxide. The optical purity of the phosphine oxide is determined by high performance liquid chromatography using an optically active column, and the above recrystallization operation is repeated until the product becomes optically pure. The thus obtained optically active phosphine oxide is then reduced by using trichlorosilane to obtain optically active OcH-BINAP.

The reaction between the complex (VII) and the optically active phosphine compound $L^1$ can usually be carried out by stirring in a solvent, e.g., tetrahydrofuran and methylene chloride, at room temperature for 20 minutes to 1 hour. The reaction between the complex (VIII) and the tertiary phosphine compound $L^2$ can usually be carried out by stirring in a solvent, e.g., tetrahydrofuran and methylene chloride, in a hydrogen gas atmosphere at room temperature for 5 to 30 hours.

The thus produced iridium-optically active phosphine complex (I) can be used as a catalyst for enantioselective syntheses either in the form of the reaction mixture as produced or after being isolated therefrom.

Examples of enantioselective hydrogenation reactions to which the complex of the present invention is applicable are described below.

Enantioselective hydrogenation of 3-oxotetrahydrothiophene in the presence of the complex (I) gives optically active 3-hydroxytetrahydrothiophene. In carrying out the reaction, the substrate, 3-oxotetrahydrothiophene, is dissolved in an appropriate solvent, e.g., methanol, tetrahydrofuran, methylene chloride, benzene, and mixtures thereof, the complex (I) is added to the substrate solution in an amount of from 1/1000 to 1/10 mole per mole of the substrate, and the reaction system is maintained at a temperature of from 10° to 50° C., and preferably around 30° C., under a hydrogen pressure of from 2 to 100 kg/cm$^2$, and preferably from 30 to 50 kg/cm$^2$.

Enantioselective hydrogenation of an $\alpha,\beta$-unsaturated ketone of formula (V) in the presence of the complex (I) yields an optically active allyl alcohol derivative of formula (VI) as illustrated by the following reaction scheme:

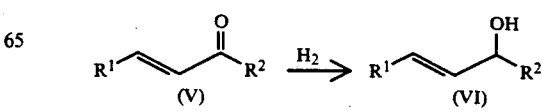

wherein $R^1$ and $R^2$ are as defined above.

Similarly to the above-mentioned enantioselective hydrogenation of 3-oxotetrahydrothiophene, this reaction is carried out in an appropriate solvent as enumerated above in the presence of from 1/1000 to 1/10 mole of the complex (I) per mole of the substrate under a hydrogen pressure of from 2 to 100 kg/cm² at a temperature of from 5° to 50° C., and preferably from 20° to 30° C.

According to the present invention, there is provided an iridium-optically active phosphine complex which exhibits high catalytic activity, achieves high optical purity, and is useful as a catalyst for various enantioselective synthesis reactions, particularly enantioselective hydrogenation reactions. By use of the complex of the present invention, optically active 3-hydroxytetrahydrothiophene and an optically active allyl alcohol derivative can be produced from 3-oxotetrahydrothiophene and an α,β-unsaturated ketone, respectively, in high purity and high yield.

The present invention is now illustrated in greater detail with reference to Reference Examples and Examples, but it should be understood that the present invention is not construed as being limited thereto.

Measuring instruments used in the Reference Examples and Examples are as follows.

$^1$H-NMR and $^{31}$P-NMR:
Model AM-400 (400 MHz) (manufactured by Bruker, Inc.)
Internal Standard: $^1$H-NMR ... tetramethylsilane
External Standard: $^-$P-NMR ... 85% phosphoric acid
Optical Rotation:
Model DIP-4 (manufactured by JASCO Inc.)
Gas chromatography (measurement of chemical purity):
Chromatograph: Shimadzu GC-9A (manufactured by Shimadzu Corporation)
Column Silica Capillary OV-101 (25 m) (manufactured by Gasukuro Kogyo K.K.)

REFERENCE EXAMPLE 1

Synthesis of [Ir(COD)((+)-BINAP)]BF₄

In a 10 ml flask with side arm whose atmosphere had been displaced with nitrogen was charged 0.9 g (1.9 mmole) of [Ir(COD)(CH₃CN)₂]BF₄ in a nitrogen atmosphere, and 200 ml of tetrahydrofuran was added thereto. Then, 20 ml of a tetrahydrofuran solution of 1.25 g (2 mmole) of (+)-BINAP was added thereto, followed by stirring at room temperature for 30 minutes. The resulting solution was concentrated to a volume of 15 ml, and the precipitated crystal was collected by filtration and dried at room temperature under reduced pressure (1 mmHg) for 6 hours to recover 1.9 g (percent yield: 95%) of the titled compound.

$^{31}$P-NMR (CD₂Cl₂) δ ppm: 15.73 (s)
$^1$H-NMR (CDCl₃) δ ppm: 1.90 (m, 2H), 2.18 (m, 4H), 2.36 (m, 2H), 4.24 (m, 2H), 4.48 (m, 2H), 6.47 (d, 2H), 6.71 (m, 4H), 6.81 (m, 2H), 7.00 (dt, 2H), 7.35 (m, 3H), 7.37 (m, 3H), 7.50–7.60 (m, 10H), 7.66 (d, 2H), 7.76 (d, 2H), 7.89 (t, 2H)

REFERENCE EXAMPLE 2

Synthesis of [Ir(COD)((-)-OcH-BINAP)]BF₄

In a 500 ml flask with side arm whose atmosphere had been displaced with nitrogen was charged 0.64 g (1.36 mmole) of [Ir(COD)(CH₃CN)₂]BF₄ in a nitrogen atmosphere, and 15 ml of tetrahydrofuran was added thereto. Then, 10 ml of a tetrahydrofuran solution of 0.86 g (1.36 mmole) of (-)-OcH-BINAP was added thereto, followed by stirring at room temperature for 30 minutes. Any insoluble matter was removed by filtration, and the filtrate was poured into 300 ml of diethyl ether, followed by allowing to stand at room temperature for 60 hours. The precipitated crystal was collected by filtration and dried at room temperature under reduced pressure (1 mmHg) to recover 1.3 g (percent yield: 93.3%) of the titled compound.

$^{31}$P-NMR (CDCl₃) δ ppm: 14.9 (s)
$^1$H-NMR (CDCl₃) δ ppm: 3.95 (m, 2H), 4.26 (m, 2H), 6.94 (d, 2H), 7.32 (q, 4H), 7.40 (d, 2H), 7.54 (m, 16H)

EXAMPLE 1

Synthesis of

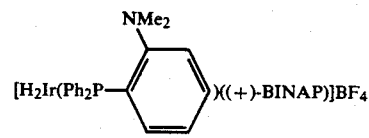

In a 50 ml flask with side arm were charged 252.2 mg (0.25 mmole) of [Ir(COD)((+)-BINAP)]BF₄ synthesized in Reference Example 1 and 80.06 mg (0.263 mmole) of

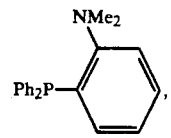

and 5 ml of tetrahydrofuran was added thereto. The reaction mixture was stirred in a hydrogen atmosphere at room temperature for 18 hours, followed by concentration to dryness to obtain 302 mg of the titled compound.

$^1$H-NMR (CD₃CN) δ ppm: -11.51 to -11.49 (m, 1H), -9.04 to -8.71 (m, 1H), 1.45 to 2.54 (6H, N-Me), 5.60 to 8.50 (46H, aromatic ring)
Elemental Analysis for C₆₄H₅₄BF₄NP₃Ir:
Calcd. (%): C 63.58; H 4.50; N 1.16
Found (%): C 63.61; H 4.39; N 1.42

EXAMPLE 2

Synthesis of

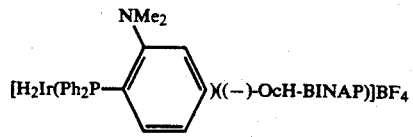

The titled complex was prepared in the same manner as in Example 1, except for replacing (+)-BINAP with (-)-OcH-BINAP.

$^1$H-NMR (CD₃CN) δ ppm: -11.73 to -11.35 (m, 1H), -9.38 to -9.06 (m, 1H), 2.04 to 2.50 (6H, N-Me), 1.60 to 2.80 (16H, methylene group), 6.00 to 8.40 (38H, aromatic ring)
Elemental Analysis for C₆₄H₆₆BF₄NP₃Ir:
Calcd. (%): C 62.95; H 5.45; N 1.15
Found (%): C 62.73; H 5.14; N 1.08

EXAMPLES 3 TO 8

The following complexes were prepared in the same manner as in Example 2, except for replacing (−)-OcH-BINAP with (+)-BINAP, (−)-Tol-BINAP or (−)-2,2′-bis{di(3,5-dimethylphenyl)phosphino}-1,1′-binaphthyl (hereinafter abbreviated as (−)-3,5-D,M-BINAP) and replacing $Ph_2P$—[phenyl-NMe$_2$]  with  PhP—[phenyl-OMe]$_2$,  P—[phenyl-NMe$_2$]$_3$, P—[phenyl-OMe]$_3$  or  PhP—[phenyl-NMe$_2$]$_2$.

EXAMPLE 3:

$[H_2Ir(P$—[phenyl-NMe$_2$]$)_3)((+)\text{-BINAP})]BF_4$

Elemental Analysis for $C_{68}H_{64}BF_4N_3P_3Ir$: Calcd. (%): C 63.06; H 4.98; N 3.24 Found (%): C 63.41; H 4.69; N 3.57

EXAMPLE 4:

$[H_2Ir(PhP$—[phenyl-OMe]$)_2)((+)\text{-BINAP})]BF_4$

Elemental Analysis for $C_{64}H_{53}BO_2F_4P_3Ir$: Calcd. (%): C 62.80; H 4.20 Found (%): C 62.71; H 4.44

EXAMPLE 5:

$[H_2Ir(PhP$—[phenyl-NMe$_2$]$)_2)((-)\text{-Tol-BINAP})]BF_4$

Elemental Analysis for $C_{70}H_{67}BF_4N_2P_3Ir$: Calcd. (%): C 64.27; H 5.16; N 2.14 Found (%): C 63.93; H 4.83; N 2.45

EXAMPLE 6:

$[H_2Ir(PhP$—[phenyl-NMe$_2$]$)_2)((-)\text{-3,5-D,M-BINAP})]BF_4$

Elemental Analysis for $C_{74}H_{75}BF_4N_2P_3Ir$: Calcd. (%): C 65.14; H 5.54; N 2.05 Found (%): C 65.01; H 5.35; N 2.41

EXAMPLE 7:

$[H_2Ir(P$—[phenyl-OMe]$)_3)((+)\text{-BINAP})]BF_4$

Elemental Analysis for $C_{65}H_{55}BF_4O_3P_3Ir$: Calcd. (%): C 62.15; H 4.41 Found (%): C 62.41; H 4.62

EXAMPLE 8:

$[H_2Ir(PhP$—[phenyl-NMe$_2$]$)_2)((+)\text{-BINAP})]BF_4$

Elemental Analysis for $C_{66}H_{59}N_2P_3BF_4Ir$: Calcd. (%): C 63.31; H 4.75; N 2.24 Found (%): C 63.53; H 4.46; H 2.19

EXAMPLE 9

Enantioselective Hydrogenation of 3-Oxotetrahydrothiophene

In a 500 ml stainless steel autoclave were charged 214.5 g (2.103 mole) of 3-oxotetrahydrothiophene and 13 g (10.5 mmole) of $[H_2Ir(PhP$—[phenyl-NMe$_2$]$)_2)((+)\text{-BINAP})]BF_4$ synthesized in Example 8 in a nitrogen atmosphere, and 200 ml of tetrahydrofuran and 43 ml of methanol were added thereto, followed by stirring at 30° C. for 45 hours under a hydrogen pressure of 50 kg/cm$^2$. The reaction mixture was concentrated, and the residue was subjected to silica gel column chromatography (eluent: hexane/benzene/ethyl acetate=70/25/10 by volume) to separate the hydrogenation product from the unreacted matter. There were recovered 146 g of the unreacted matter and 63 g of 3-hydroxytetrahydrothiophene (conversion: 31.8%; theoretical percent yield: 93.8%).

$[\alpha]_D^{25}$: +9.2° (c=2.7, CHCl$_3$)

Optical purity: 63.2 %ee

EXAMPLE 10

In a 100 ml stainless steel autoclave were charged 3 ml (35.1 mmole) of 3-oxotetrahydrothiophene and 0.121 g (0 176 mmole) of $[Ir(Ph_2P$—[phenyl-NMe$_2$]$))((+)\text{-BINAP})]BF_4$ synthesized in Example 2 in a nitrogen atmosphere, and 3 ml of tetrahydrofuran and 1 ml of methanol were added thereto. The mixture was stirred at 30° C. under a hydrogen pressure of 50 kg/cm² for 45 hours, and the reaction mixture was worked up in the same manner as in Example 9 to obtain 0.84 g of 3-hydroxytetrahydrothiophene (conversion: 30.1%; theoretical percent yield: 93.5%).

$[\alpha]_D^{25}$: +9.6° (c=2.65, CHCl₃)

Optical purity: 65.7 %ee

EXAMPLE 11

In the same manner as in Example 9, except for using

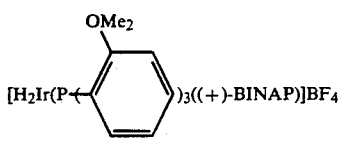

synthesized in Example 7 as a catalyst, 3-hydroxytetrahydrothiophene having an optical purity of 61.1 %ee was obtained at a conversion of 17.1% and a theoretical percent yield of 93%.

EXAMPLE 12

In a 200 ml stainless steel autoclave were charged 5 g (34.2 mmole) of benzalacetone and 0.213 g (0.171 mmole) of

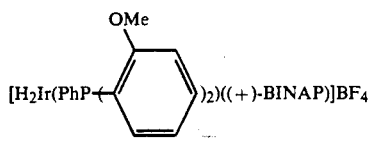

synthesized in Example 4, and 3 ml of tetrahydrofuran and 2 ml of methanol were added thereto, followed by allowing the mixture to react at 30° C. under a hydrogen pressure of 50 kg/cm² for 45 hours. The solvent was removed by distillation under reduced pressure (10 mmHg), and the reaction product was analyzed by GLC (PEG HT, 25 m, produced by Gasukuro Kogyo K.K.) to find the conversion to be 34.5%. The product was separated into the unreacted ketone and the hydrogenation product by silica gel column chromatography (eluent: hexane/ethyl acetate=4/1 by volume) to obtain 1.73 g of 4-phenyl-3-buten-2-ol having a purity of 89%. $[\alpha]_D^{25}$: +18.1° (c=5, CS₂).

The resulting allyl alcohol was found to have an optical purity of 76.5 %ee as measured by using CHIRALCEL OD (eluent: hexane/isopropanol=9/1 by volume) at a flow rate of 0.5 ml/min and at a UV detection wavelength of 254 nm.

EXAMPLE 13

In a 100 ml stainless steel autoclave were charged 5 g (34.2 mmole) of benzalacetone and 0.204 g (0.171 mmole) of

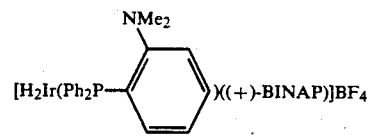

synthesized in Example 1, and the mixture was allowed to react in the same manner as in Example 12 to obtain 1.34 g of 4-phenyl-3-buten-2-ol having a purity of 70% and an optical purity of 70.3 %ee at a conversion of 26.7%.

EXAMPLE 14

In the same manner as in Example 12, except for using

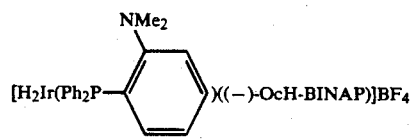

synthesized in Example 2, 1.68 g of an allyl alcohol having a purity of 90% and an optical purity of 68 %ee was obtained at a conversion of 30%.

While the invention has been described in detail and with reference to specific examples thereof, it will be apparent to one skilled in the art that various changes and modifications can be made therein without departing from the spirit and scope thereof.

What is claimed is:

1. A process for producing an optically active allyl alcohol derivative represented by formula (VI):

wherein R¹ represents a phenyl group which may be substituted and R² represents an alkyl group, comprising enantioselective hydrogenating an α,β-unsaturated ketone represented by formula (V):

wherein R¹ and R² are as defined above, in the presence of an iridium-optically active phosphine complex represented by formula (I):

wherein L¹ represents an optically active phosphine compound represented by formula (II):

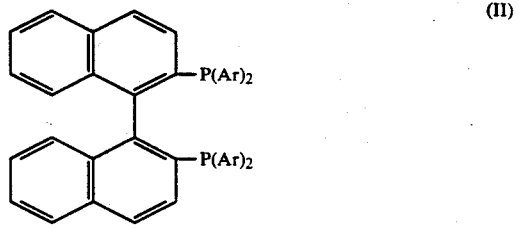

wherein Ar represents a phenyl group or a p- and/or m-lower alkyl-substituted phenyl group, or formula (III):

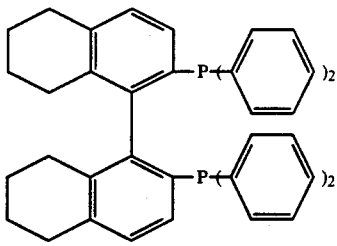

(III)

L² represents a tertiary phosphine compound represented by formula (IV):

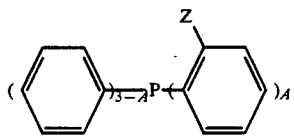

(IV)

wherein Z represents a lower alkoxy group or a di-lower alkylamino group; and A represents an integer of from 1 to 3; Y represents $BF_4$, $PF_6$, $ClO_4$, or $BPh_4$, wherein Ph represents a phenyl group.

2. A process for producing an optically active allyl alcohol derivative as in claim 1, wherein the complex of formula (I) is present in an amount of 1/1,000 to 1/10 mol per mol of substrate.

3. A process for producing an optically active allyl alcohol derivative as in claim 1, wherein the hydrogenating is carried out at a temperature of 5° to 50° C.

4. A process for producing an optically active allyl alcohol as in claim 3, wherein the hydrogenating is carried out at a temperature of 20° to 30° C.

5. A process for producing an optically active allyl alcohol derivative as in claim 1, wherein the hydrogenating is carried out under a hydrogen pressure of from 2 to 100 kg/cm².

6. A process for producing an optically active allyl alcohol derivative as in claim 1, wherein the complex represented by formula (I) is present in an amount of 1/1,000 to 1/10 mol per mol of substrate, the hydrogenating is carried out at a temperature of 5° to 50° C. and the hydrogenating is carried out under a hydrogen pressure of 2 to 100 kg/cm².

7. A process for producing an optically active allyl alcohol derivative as in claim 1, wherein the substrate is dissolved in a solvent selected from the group consisting of methanol, tetrahydrofuran, methylene chloride, benzene and mixtures of any two or more of the above solvents.

8. A process for producing an optically active allyl alcohol derivative as in claim 1, wherein $R^2$ is a methyl group.

* * * * *